United States Patent
Pepper

(10) Patent No.: US 6,696,692 B1
(45) Date of Patent: Feb. 24, 2004

(54) PROCESS CONTROL METHODS FOR USE WITH E-BEAM FABRICATION TECHNOLOGY

(75) Inventor: David M. Pepper, Malibu, CA (US)

(73) Assignee: HRL Laboratories, LLC, Malibu, CA (US)

( * ) Notice: Subject to any disclaimer, the term of this patent is extended or adjusted under 35 U.S.C. 154(b) by 66 days.

(21) Appl. No.: 09/707,444

(22) Filed: Nov. 6, 2000

(51) Int. Cl.⁷ .............................................. H01J 37/08
(52) U.S. Cl. .............................. 250/492.21; 250/443.1; 250/495.1; 374/45
(58) Field of Search .................. 250/492.21, 492.2, 250/495.1, 310, 311, 443.1; 374/45

(56) References Cited

U.S. PATENT DOCUMENTS

| | | | |
|---|---|---|---|
| 4,468,136 A | * 8/1984 | Murphy et al. | 250/334 |
| 4,579,463 A | * 4/1986 | Rosencwaig et al. | 356/432 |
| 4,636,088 A | * 1/1987 | Rosencwaig et al. | 374/5 |
| 4,710,030 A | 12/1987 | Tauc et al. | 356/432 |
| 4,752,140 A | * 6/1988 | Cielo et al. | 356/484 |
| 4,799,392 A | * 1/1989 | Wilson et al. | 73/865.9 |
| 4,860,224 A | 8/1989 | Cashell et al. | 364/551.01 |
| 4,874,251 A | * 10/1989 | Thomas et al. | 250/334 |
| 5,020,920 A | * 6/1991 | Gopalsami et al. | 324/630 |
| 5,432,119 A | 7/1995 | Le et al. | |
| 5,483,068 A | * 1/1996 | Moulton et al. | 250/340 |
| 5,574,280 A | * 11/1996 | Fujii et al. | 250/309 |
| 5,582,485 A | * 12/1996 | Lesniak | 250/330 |
| 5,656,811 A | * 8/1997 | Itoh et al. | 250/309 |
| 5,760,904 A | 6/1998 | Lorraine et al. | |
| 5,770,861 A | * 6/1998 | Hirose et al. | 250/306 |
| 5,894,058 A | * 4/1999 | Hatakeyama et al. | 430/313 |
| 5,900,935 A | 5/1999 | Klein et al. | |
| 5,966,626 A | * 10/1999 | Lo et al. | 438/530 |
| 6,049,220 A | * 4/2000 | Borden et al. | 324/765 |
| 6,419,387 B1 | * 7/2002 | Legrandjacques et al. | 374/5 |

FOREIGN PATENT DOCUMENTS

| | | | |
|---|---|---|---|
| JP | 59-177846 | 10/1984 | |
| JP | 59177846 A | * 10/1984 | H01J/37/28 |
| WO | 87/00632 | 1/1987 | |

OTHER PUBLICATIONS

Smith et al, "Ion Implant monitoring with thermal wave technology", Sep. 1985, Appl. Phys. Lett. 47 (6), pp. 584–586.*

Coy, J.A. et al., "Asymmetric Interdigitated Metal–semiconductor–metal Contacts for Improved Adaptive Photoinduced–electromotive–force Detectors", Optical Society of America, vol. 17, No. 5, May 2000, pp. 697–704.

Dunning, G.J. et al., "Robust Laser–Based Ultrasound Sensor Using Integrated Photo–Induced EMF Detection and Time–Delay Interferometer", Review of Progress in Quantitative Nondestructuive Evaluation, vol. 16, New York, 1997, pp. 579–586.

Pepper, David M. et al., "Materials Inspection and Process Control Using Compensated Laser Ultrasound Evaluation (CLUE™) : Demonstration of a Low–Cost Laser–Ultrasonic Sensor", Lasers as Tools for Manufacturing of Durable Goods and Microelectronics, Society of Photo–Optical Instrumentation Engineers, vol. 2703, Washington, 1996, pp. 91–102.

* cited by examiner

Primary Examiner—John R. Lee
Assistant Examiner—Kalimah Fernandez
(74) Attorney, Agent, or Firm—Ladas & Parry

(57) ABSTRACT

A method and apparatus for e-beam fabrication of a workpiece. A surface of the workpiece is impinged with a e-beam during a manufacturing step in the manufacture of the workpiece. Simultaneously, the workpiece is optically sensed using thermal-wave imaging and/or ultrasound imaging techniques for process control of the workpiece. The e-beam impinging the workpiece in the manufacture of the workpiece provides substantially all the energy needed to be added to the workpiece to perform the optical sensing of the workpiece.

25 Claims, 2 Drawing Sheets

PROCESS CONTROL METHODS FOR USE WITH E-BEAM FABRICATION TECHNOLOGY

TECHNICAL FIELD

The present invention relates to the use of non-contact, long-standoff, optically based inspection techniques for on-line inspection and process control of the e-beam manufactured workpieces, including composites and other advanced materials.

BACKGROUND OF THE INVENTION

The present invention allows for the real-time inspection during e-beam processing of composites and related materials. In the prior art, such composite-based materials were routinely fabricated in so-called autoclave systems, which are size-limited and tend to be slow. More recently e-beams have been used to locally treat these materials by localized heating.

In the prior art, thermal wave imaging (TWI) has been used as a diagnostic technique to inspect workpieces, including composites and other advanced materials. See U.S. Pat. No. 4,874,251 to Thomas et al.

In the prior art, laser-based ultrasound (LBU) has also been used as a diagnostic technique to inspect what pieces, including composites and other advanced materials. See, for example, U.S. Pat. No. 5,760,904 to Lorraine et al.

The disclosures of U.S. Pat. Nos. 4,874,251 and 5,760,904 are hereby incorporated herein by reference.

E-beam processing holds a lot of promise since it can be used to manufacture large-area components at higher rates and with less energy than prior art autoclave systems. Given this robust manufacturing tool, the need for adequate process control becomes a critical issue. The use of the LBU and TWI for this process-control provides a number of advantages in that the e-beam used in the manufacture of a workpiece can also be used as an energy source for the LBU and/or TWI non destructive testing applications.

The present invention relates to a method of process control for e-beam fabrication of a workpiece, the method including the steps of: (i) impinging the workpiece with a e-beam during a manufacturing step in the manufacture thereof and (ii) simultaneously optically sensing the workpiece using thermal-wave imaging and/or ultrasound imaging techniques for process control, wherein the e-beam impinging the workpiece in accordance with step (i) above provides substantially all the energy needed to be added to the workpiece to perform the optical sensing of step (ii) above.

The present invention can greatly enhance the manufacturability (quality assurance, reliability, reproducability, etc.) for e-beam fabrication since the in-situ LBU and TWI diagnostics can yield quality assurance information at each step (e.g. as each pre-preg layer is processed) as well as provide feedback control to the e-beam to optimize its parameters (energy, focus, scan rate, etc.) for rapid and high quality e-beam manufacturing.

DETAILED DESCRIPTION OF THE INVENTION

Figure 1:
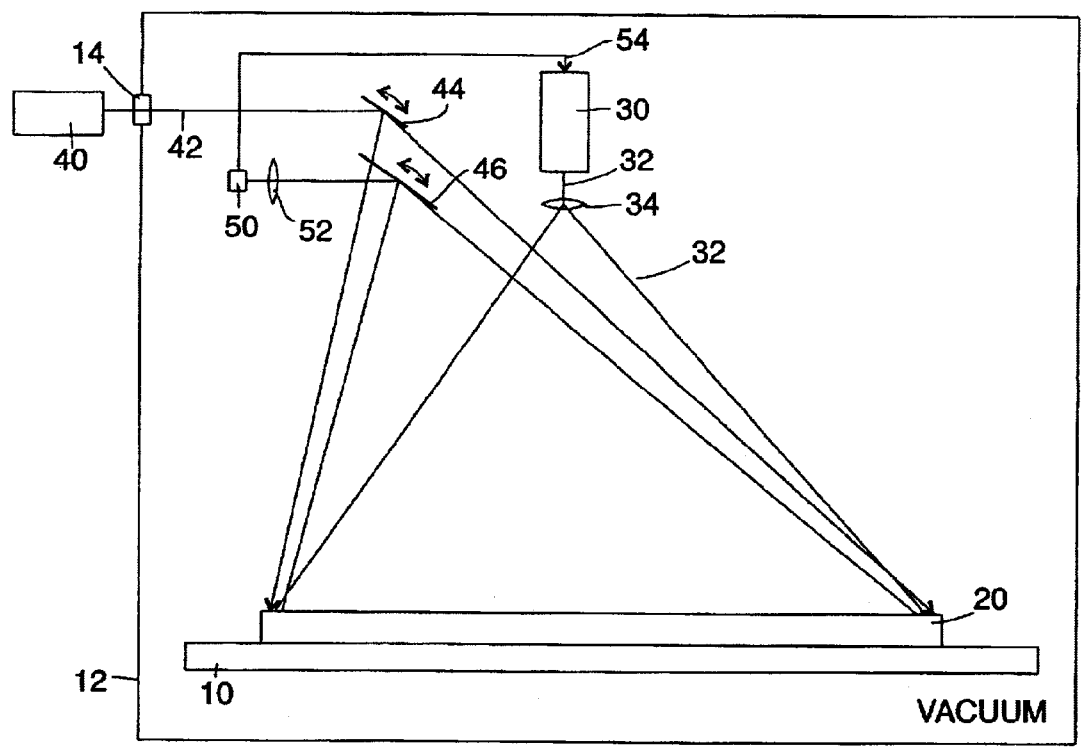
FIG. 1 is a schematic drawing of a first embodiment of the present invention which utilizes LBU to examine the workpiece as it is being processed by an e-beam.

The present invention involves the use of two different, yet complementary, all-optical inspection tools, which can be used separately or combined to advantage, both with the potential for real-time, single-pixel or full-frame inspection during the manufacture of such composites and materials using e-beam techniques. Both approaches are optically based and are long-standoff, remote and nondestructive. These inspection tools are laser-based ultrasound (LBU) and themal-wave imaging (TWI). They are both intertwined, in that the generation of transient ultrasound in a workpiece is typically accompanied by a corresponding thermal transient, and vice versa. Both the acoustic and a thermal excitations can be used to probe materials for elastic (surface and internal) properties and hidden or buried defects, such as delamination, impact damage, etc. These excitations are manifested on the surface of the workpiece by several signatures: small surface displacements (in the case of ultrasound) and temperature variations on the surface (in the case of thermal-wave imaging). The time dependence and the spatial variation of the signatures can reveal internal features or defects of interest for the process control of workpieces, including advanced composites. The interval features or defects which can be detected include internal delaminations, micro cracks, and cure cycle phases (liquefication, gelation, solidification, et cetera).

Prior art LBU and TWI diagnostic techniques involve a modulated excitation source (e.g., a pulse laser or flash lamp), and an optical sensing system. In terms of the detection techniques, LBU typically requires an optical interferometer for the sensing of the ultrasonically induced surface displacements (in the range of nanometers at megahertz rates), whereas thermal-wave imaging typically employs a sensitive infrared viewer to sense the thermal surface variations (in the range of degrees at kilohertz rates). In accordance with the present invention, the e-beam parameters very closely match the optical excitation parameters required for both LBU and TWI generation. For example, the incident e-beam energy density at the workpiece is typically on the order of 1 $J/km^2$, which is on the order of, or greater than, typical laser-beam parameters (typically about 10 to 100 $mJ/cm^2$, for either the thermoelastic or the ablative excitation regimes). Similarly, the e-beam pulse duration is on the order of 50 nanoseconds or greater (which would efficiently couple into the desired ultrasonic modes to probe these materials), which is compatible to typical LBU generation laser pulse lengths (10 nanoseconds to 1 microsecond). In a similar vein, the spot sizes are compatible (about a few millimeters to a few centimeters) as are the pulse repetition of rates (about 10 Hz to 1 kHz).

The temperature changes that occur during e-beam processing are typically within a few degrees, which is on the same order as is typical in TWI systems. Finally, given the raster scan rates of e-beam system, the optical sensing can be performed with the same mesh size as that of the e-beam processing step-size, thereby effectively matching the length and time scales of the overall manufacturing system. As such, no processing delay need occur for the sensing and inspection to take place in accordance with the present invention. Since the LBU and TWI diagnostic techniques are optically based, the imaging path and the e-beam propagation trajectory can share a common path, if needed in any particular application.

Given the similarities in the parameters as set forth above, both ultrasound, as well as thermal-wave imaging, can be obtained directly during e-beam processing. Therefore, the sensing schemes (LBU and TWI) are, in essence, passive, and the excitation mechanism is inherent in the processing e-beam itself. As such, in principle, no additional excitation source should be required to generate the ultrasound and/or thermal modes used for LBU and/or TWI non-destructive testing. Of course, if needed, auxiliary laser beams or lower energy, secondary e-beams can be used to help excite the ultrasound and thermal modes for spot checks, either at the same location as the primary e-beam used in the manufacturing process, or spatially separated after the primary e-beam processing. However, the primary e-beam will usually provide substantially all (i.e. at least 95%) of the energy required to generate the ultrasound and/or thermal modes used for LBU and/or TWI non-destructive testing, so little or no additional energy input is needed. Moreover, both LBU and TWI can be employed directly, thereby forming a so-called sensor suite for improved diagnostic information. Of course, LBU or TWI can be employed independently, if desired.

FIG. 1 depicts an embodiment of the present invention which utilized TWI for inspection of a workpiece 20. Turning to FIG. 1, the workpiece is shown as being disposed on a work surface 10 in a vacuum containment 12. An e-beam gun is depicted at numeral 30 and the e-beam emitted thereby is identified by numeral 32. An appropriate focussing lens or apparatus 34 is utilized to cause the emitted e-beam to focus on and impinge the exposed surface of workpiece 20 and an appropriate means is utilized to control where the focussed e-beam spot impinges the surface of the workpiece 20. By way of example, the workpiece 20 could be a laminate which is undergoing e-beam processing to fuse the laminations thereof together and the workpiece could be moved relative to the e-beam gun by an appropriate transport means or the direction of the beam.

A laser 40 is used to illuminate a portion of the surface at the same time that it is undergoing e-beam processing. The laser 40 emits a probe laser beam which is identified by numeral 42. The laser beam 42 is directed to the surface of the workpiece 20 by a beam steering apparatus such as moving, rotatably-mounted mirror or other means 44 for controlling the direction of the laser beam 42 such as a fiber optic bundle. The laser beam 42 is reflected from the surface of the workpiece and is collected and directed to a LBU receiver 50 by, for example, a moving, rotatably-mounted mirror or other means 46, for controlling the reception and/or direction of the reflected laser beam in combination with a lens or other focussing means 52. Alternatively, a fiber optic bundle could be used to collect the reflected laser light and transport it to receiver 50.

A fiber optic bundle can also be used to direct the probe laser beam 42 across the workpiece 20. In such an embodiment a complete fiber-based system can be used for optical delivery of the probe beam 42 and the collection of the laser light reflected from the surface of the workpiece 20. Robot manipulators can then be used to direct a fiber head carrying the fiber bundles adjacent the surface of the workpiece 20 to probe desired locations on the workpiece 20.

The sensor 50 preferably operates as part of a feed back loop 54 for controlling the e-beam gun and to control where the focussed e-beam spot impinges the surface of the workpiece 20. Thus when a defect is detected (for example in the case of fusing laminations together, the defect might well be a place where adjacent laminations are insufficiently fused), the e-beam is directed to reheat the region with the defect. Alternatively, the feedback loop 54 could be used to speed up the movement of the beam if the workpiece were being heated more than is necessary or to slow down the movement of the beam if the workpiece were being heated less than is necessary. The feedback loop 54 preferably has sufficient computational power to detect defect regions and/or whether the workpiece is being over or under heated and to control the path of the e-beam to traverse again those regions which appear to be defective according to the LBU receiver 50 or to change the dwell time of the e-beam to apply the correct amount of energy to the workpiece.

The e-beam apparatus is preferably installed in an enclosure 12 so that the workpiece may be worked in a vacuum environment. In order to reduce shielding which would otherwise be used on the laser 40, it is preferably placed outside enclosure 12 and its beam 42 is allowed to enter the enclosure via a air tight quartz window or port 14. The LBU receiver 50 may similarly be placed outside enclosure 12 to avoid the radiation environment inside enclosure 12 and, if a fiber optic bundle is used to collect the reflected laser light, that makes it rather convenient to place the LBU receiver 40 outside enclosure 12

The e-beam gun 30 emits pulses of energy having a duration, for example, of 10 nsec per pulse, an energy between 100 mj/cm$^2$ and 100 J/cm$^2$ with a spot size diameter at the surface of the workpiece of 1 to 30 mm. The laser 40 operates at a significantly reduced power level compared to the e-beam gun 30 and it might only contribute 1% or less of the energy impinging the surface of the workpiece 20. Laser 40 can be a continuous wave (CW) laser or it can be pulsed, in which can the length of a pulse should be sufficient to detect ultrasonic acoustic events in the workpiece 20 caused by the e-beam 32. The output of laser 40 is preferably adjusted so that its laser 42 does not modify the workpiece 20; rather laser 40 is preferably a passive, non-intrusive, optically sensing probe.

The heating of the workpiece may cause a chemical reaction to occur which is exothermic, that is the workpiece itself may generate some heat under the influence of the e-beam. In any event the heat generated by the e-beam in combination with any exothermic heating of the workpiece due to a chemical reaction caused by the e-beam is sufficient to provides substantially all the energy needed to be added to the workpiece to perform the optical sensing thereof. The energy contributed to the workpiece 20 by the laser 40 is negligible in comparison to the energy contributed by the e-beam gun 30.

The LBU non destructive testing envisioned by the present invention does not require a powerful laser to excite the workpiece 20, but rather the ultrasonic testing can rely substantially, if not entirely, on energy imparted by the e-beam 32 used in a conventional manufacturing processes on the workpiece 20 to supply the needed energy into the workpiece 20 for the testing to take place. As such, LBU in the context of the present invention, is a bit of a misnomer. Perhaps this non-destructive ultrasonic test should better be referred to as e-beam based ultrasound or just EBU for short. The EBU, when performed as a part of the present invention, can be identical to prior art LBU non-destructive testing except that the (1) the energy source is different and (2) the timing of performance of the non-destructive test is different since it occurs simultaneously with e-beam process steps used in manufacturing operations performed on a workpiece 20.

In accordance with the present invention, process related information can be obtained during the manufacturing process, without having to complete the overall process, or without having to remove the workpiece from the enclosure 12. As such, the process information is collected simultaneously as energy is supplied to the workpiece 20 by an e-beam 32 used in the manufacturing process. Therefore, in-process, servo-controlled control systems, with immediate detection of flaws in the workpiece (due to internal defects or changes in the e-beam parameters, etc.) will now be a reality. This can enable one to quickly and efficiently detect and modify the manufacturing system early in the manufacturing process, thereby saving time, cost, materials, labor,etc.

Figure 2:
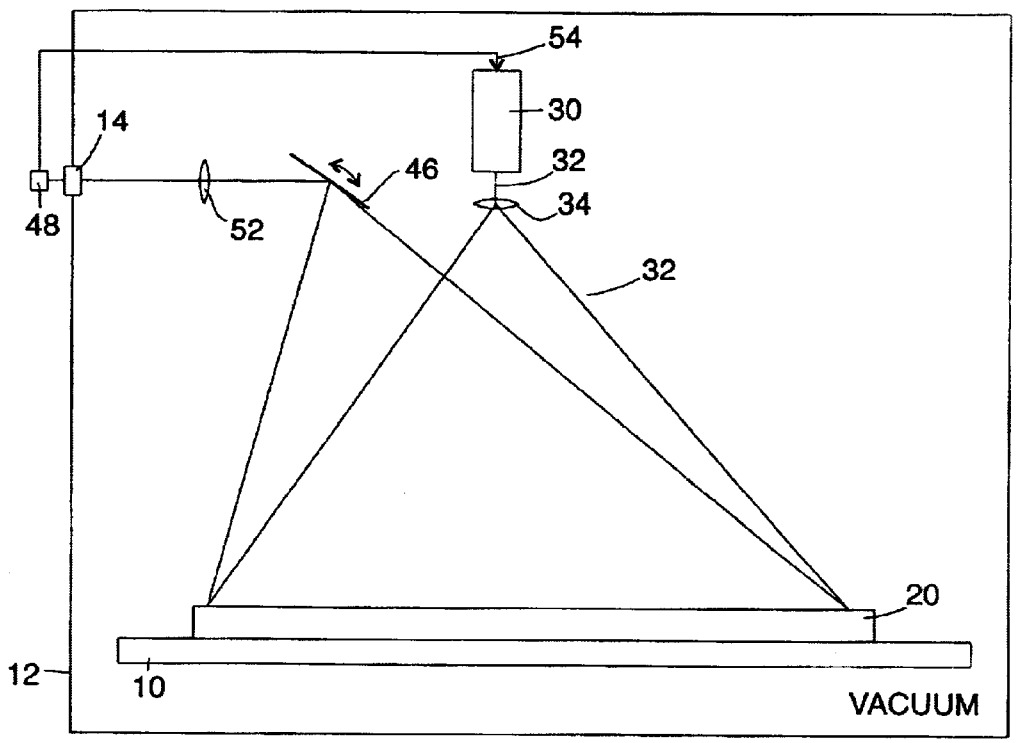
FIG. 2 is a schematic drawing of a second embodiment of the present invention which utilizes TWI to examine the workpiece as it is being processed by an e-beam.

FIG. 2 depicts a TWI embodiment of the invention. In this embodiment an infrared camera 48 is used to examine a relatively large swath of area (typically a couple of centimeters square to tens of centimeters square) on the workpiece 20. The infrared camera 48 examines the swath and, depending on its frame rate, it periodically updates pixel data reflecting a temperature or emissivity profile of that portion of the surface of the workpiece represented by the swath of pixel data. This temperature profile data can be used to detect defects, for example, in workpiece 20. In the case of a laminated workpiece, for example, a defect would include a region where two laminations had not been properly bonded one to another. Such a region will appear as a "hot spot" on the surface of the workpiece to the infrared camera 48. The "hot spot" might only be a fraction of one degree (Centigrade or Fahrenheit) hotter than the surrounding areas, so the infrared camera 48 should be sensitive to rather small temperature variations on the surface of workpiece 20.

As in the case of LBU, a feedback loop 54 is preferably used to provide for real time correction of problem areas occurring in the workpiece 20. The feedback loop preferably includes a video processor to review the large number of pixels which make up a swath of data.

Comparing FIG. 2 with FIG. 1 it will be noted that most of the components and/or elements are identified by a common reference numeral between the two figures. As such, the reader is directed to the discussion of the first embodiment of FIG. 1 for a discussion regarding such elements and/or components. In the discussion of the first embodiment it was mentioned that the receiver 50 could be placed outside enclosure 12 to reduce the radiation environment in which it operates (and hence to reduce any need to radiation harden its own enclosure). In this second embodiment, the sensing element, namely camera 48, is shown outside the enclosure. It could, of course, be placed inside of the enclosure if it is sufficiently robust to tolerate the high radiation environment caused by the e-beam gun 30.

An important advantage of the present invention is that EBU and TWI diagnostic techniques are compatible with the high background radiation levels which can occur in e-beam manufacturing systems in the enclosure 12. As such, the use of optical techniques of EBU and TWI to sense ultrasonic and thermal variations in the workpiece is well suited for this application. Off-the-shelf optical beam detectors (such as articulated mirrors and optical fibers) and imaging components can be used to inspect the same part of the workpiece that is being processed by the e-beam. The sensing elements (receiver 50 and camera 48) may need to be either radiation hardened or placed outside the enclosure 12. The optical systems disclosed herein can sense regions directly at the location of where the e-beam impinges the surface of the workpiece or can sense a portion of the workpiece 20 immediately opposite were the e-beam is impinging same or downstream a short distance after the e-beam processing has occurred.

Figure 3:
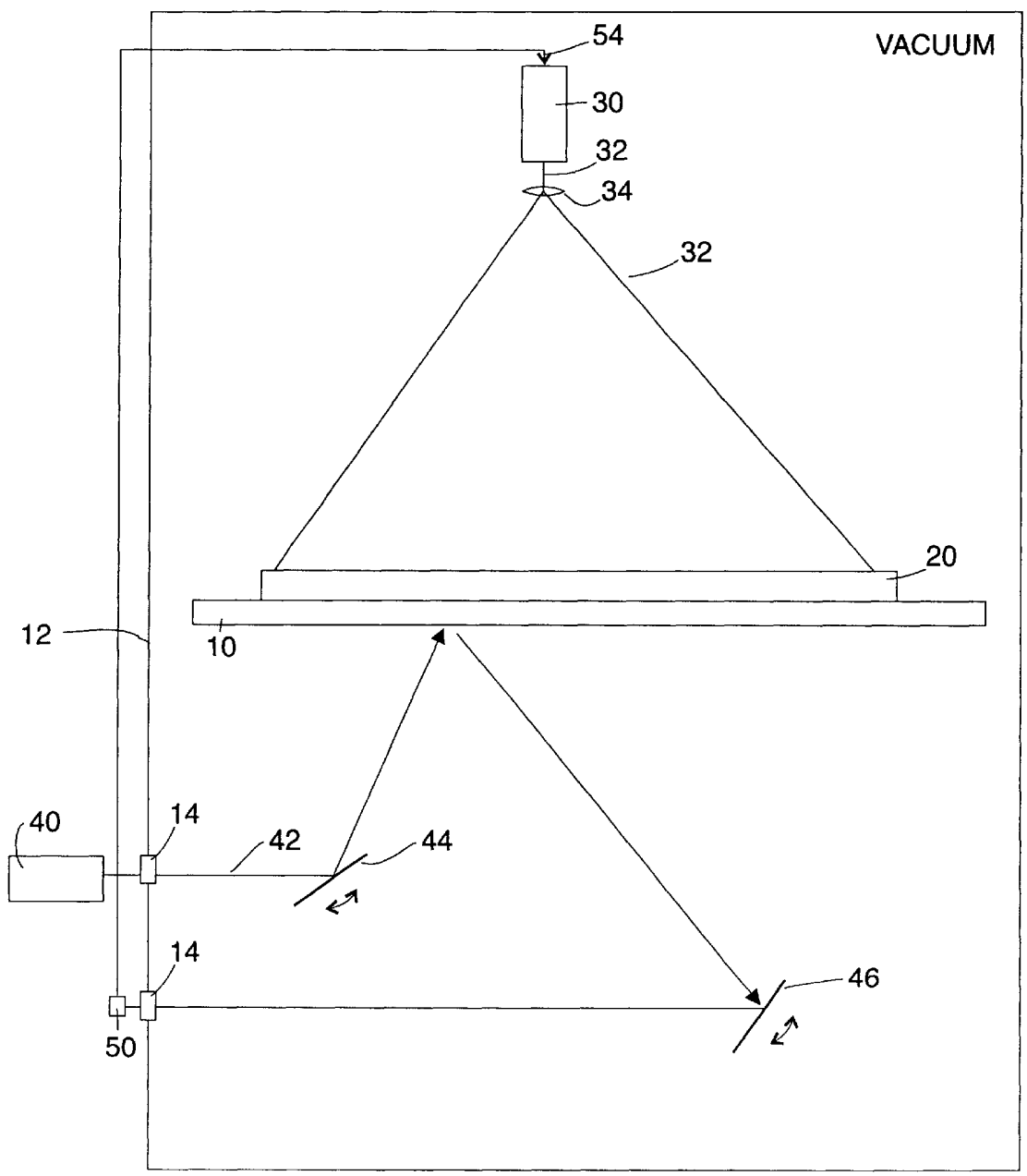
FIG. 3 is a schematic drawing of a third embodiment of the present invention which utilizes LBU to examine the workpiece as it is being processed by an e-beam on a side opposite from the side being worked by the e-beam.

It should be noted that a single-pixel inspection configuration can be utilized or a more global (i.e. full-frame) diagnostic over a larger area of the workpiece can be realized. Additionally, the optical inspection can take place either on the same surface as the impinging e-beam, or on an opposite surface, or on both surfaces, depending upon the specific system needs and system constraints. An embodiment showing testing occurring on a side opposite to the side impinged by the e-beam 32 is shown by FIG. 3. The numerals used for the components are the same as the case of the embodiment of FIG. 1. In this embodiment surface 10 is preferably transparent (so that is it transmissive of the laser beam 42 and the reflected laser light) or alternatively is a thin platen (so that it can efficiently transmit ultrasound or thermal variations, with minimal absorption or dispersion, to its surface which is illuminated by laser 40).

The present invention provides an inspection tool which is very robust, and reconfigurable, and flexible. Given that the inspection can be accomplished on a layer-by-layer basis, system adjustments (e-beam parameters, such as spot size, raster scan rate, energy, etc.) can be made as needed to optimize the layer-by-layer basis. Finally, being in a high-radiation environment, the laser beams can be directed onto the part through optical fibers, which can be radiation hardened, as well as installed through radiation-shielded pathways in the processing facility.

Having described the invention with respect to a preferred embodiment thereof, modification will now doubtlessly suggests itself to those skilled in the art. As such, the invention is not to be limited to the embodiments described above, except as required by the appended claims.

What is claimed is:

1. A method of process control for e-beam fabrication of a workpiece, said method including the steps of:
   (a) impinging a surface of the workpiece with an e-beam during a manufacturing step in the manufacture thereof during which manufacturing step the workpiece is modified by the e-beam, and
   (b) optically sensing the workpiece using thermal-wave imaging and/or ultrasound imaging techniques for process control,
       wherein the e-beam impinging the workpiece in accordance with step (a) above provides substantially all the energy needed to be added to the workpiece to perform the optical sensing of step (b) above.

2. The method of claim 1 wherein the e-beam causes an exothermic chemical reaction to occur in the workpiece, which exothermic reaction generates energy, which contributes, in turn, to the energy needed to be added to the workpiece to perform the optical sensing of step (b) above.

3. The method of claim 1 wherein the e-beam comprises pulses of energy having a duration on the order of 10 nsec per pulse, an energy between 100 mj/cm$^2$ and 100 J/cm$^2$ and a spot size diameter at a surface of the workpiece of 1 to 10 mm.

4. A method of process control for e-beam fabrication of a workpiece, said method including the steps of:
   (a) impinging a surface of the workpiece with an e-beam during a manufacturing step in the manufacture thereof, and
   (b) optically sensing the workpiece using thermal-wave imaging and/or ultrasound imaging techniques for process control, wherein the e-beam impinging the workpiece in accordance with step (a) above provides substantially all the energy needed to be added to the workpiece to perform the optical sensing of step (b) above and wherein the e-beam is controlled by a feedback loop based on data obtained during step (b) above.

5. The method of claim 4 wherein the optically sensing step (b) includes sensing infrared light emanating from the surface of the workpiece.

6. The method of claim 4 wherein the optically sensing step (b) includes:
   (b1) illuminating at least a portion of the surface of the workpiece with a low power laser beam, the low power laser beam having a power output significantly less than the power of the e-beam; and
   (b2) sensing reflected laser light from the surface of the workpiece.

7. The method of claim 1 wherein the step (b) of simultaneously optically sensing the workpiece occurs at a surface related to said workpiece.

8. The method of claim 7 wherein the related surface is the surface of a support structure which is transmissive of energy at a surface of the workpiece.

9. An apparatus for e-beam fabrication of a workpiece, said apparatus including:
   an e-beam generator for generating an e-beam;
   a direction control apparatus for directing the e-beam to impinge a surface of the workpiece with the e-beam;
   an optical sensor for simultaneously optically sensing the workpiece; and
   a feedback loop for controllably coupling the optical sensor to the e-beam generator and to the direction control apparatus for affecting where on the surface of the workpiece that the e-beam is directed,
   wherein the e-beam impinging the workpiece provides substantially all the energy needed to be added to the workpiece to perform the optical sensing by the optical sensor.

10. The apparatus of claim 9 wherein the e-beam causes an exothermic chemical reaction to occur in the workpiece, which exothermic reaction generates energy which contributes to the energy needed to be added to the workpiece to perform the optical sensing by the optical sensor.

11. The apparatus of claim 9 wherein the e-beam generator generates pulses of energy having a duration on the order of 10 nsec per pulse, an energy between 100 mj/cm$^2$ and 100 J/cm$^2$ and a spot size diameter at a surface of the workpiece of 1 to 10 mm.

12. The apparatus of claim 9 wherein the optical sensor includes a camera for sensing infrared light emanating from the surface of the workpiece.

13. The apparatus of claim 9 wherein the optical sensor includes:
   a low power laser for illuminating at least a portion of the surface of the workpiece with a low power laser beam, the low power laser beam having a power output significantly less than the power of the e-beam; and
   a receiver for sensing laser light reflected from the surface of the workpiece.

14. The apparatus of claim 13 wherein the workpiece is supported by a support surface which is transmissive of optical energy having a wavelength of the laser beam emitted by said low power laser.

15. An apparatus for e-beam fabrication of a workpiece, said apparatus including:
   an e-beam generator for generating an e-beam for performing an e-beam fabrication operation on the workpiece;
   a direction control apparatus for directing the e-beam to impinge a surface of the workpiece with the e-beam;
   an optical sensor for simultaneously optically sensing the workpiece, the optical sensor including (i) a low power laser for illuminating at least a portion of the surface of the workpiece with a low power laser beam or of a surface associated with the workpiece, the low power laser beam having a power output significantly less than the power of the e-beam and (ii) a receiver for sensing laser light reflected from the surface of the workpiece;
   wherein the e-beam impinging the workpiece provides substantially all the energy needed to be added to the workpiece to perform the optical sensing by the optical sensor.

16. The apparatus of claim 15 wherein the workpiece is supported by a support surface which is transmissive of sonic energy, said support surface being associated with said workpiece for the transmission of sonic energy for detection by the receiver detecting the laser beam emitted by said low power laser, illuminating said support surface and reflected therefrom.

17. A method of process control for e-beam fabrication of an object, said method including the steps of:
   (a) impinging a surface of the object with an e-beam during a manufacturing step, the e-beam modifying the object, and
   (b) optically sensing the object using thermal-wave imaging and/or ultrasound imaging techniques for process control,
   wherein the e-beam impinging the object in accordance with step (a) above modifies the object and provides substantially all the energy needed to be added to the object to perform the optical sensing of step (b) above.

18. The method of claim 17 wherein the e-beam causes an exothermic chemical reaction to occur in the object, which exothermic reaction generates energy, which contributes, in turn, to the energy needed to be added to the object to perform the optical sensing of step (b) above.

19. The method of claim 17 wherein the object is a laminate.

20. The method of claim 17 wherein the e-beam comprises pulses of energy having a duration on the order of 10 nsec per pulse, an energy between 100 mj/cm$^2$ and 100 J/cm$^2$ and a spot size diameter at a surface of the object of 1 to 10 mm.

21. The method of claim 17 wherein the e-beam is controlled by a feedback loop based on data obtained during step (b) above.

22. The method of claim 21 wherein the optically sensing step (b) includes sensing infrared light emanating from the surface of the object.

23. The method of claim 21 wherein the optically sensing step (b) includes:
   (b1) illuminating at least a portion of the surface of the object with a low power laser beam, the low power laser beam having a power output significantly less than the power of the e-beam; and
   (b2) sensing reflected laser light from the surface of the object.

24. The method of claim 17 wherein the step (b) of simultaneously optically sensing the object occurs at a surface related to said object.

25. The method of claim 24 wherein the related surface is the surface of a support structure which is transmissive of energy at a surface of the object.

* * * * *